(12) United States Patent
Alvey et al.

(10) Patent No.: US 8,622,974 B2
(45) Date of Patent: Jan. 7, 2014

(54) PLUNGER-DRIVEN FEEDING TUBE DELIVERY DEVICE AND METHODS

(75) Inventors: John D. Alvey, Evansville, IN (US); Marc S. Velmer, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 346 days.

(21) Appl. No.: 13/031,298

(22) Filed: Feb. 21, 2011

(65) Prior Publication Data
US 2012/0215205 A1   Aug. 23, 2012

(51) Int. Cl.
*A61M 5/00* (2006.01)
*A61M 37/00* (2006.01)
*A61M 5/315* (2006.01)

(52) U.S. Cl.
USPC ............... 604/191; 604/82; 604/92; 604/181; 604/187; 604/218; 604/220; 604/223

(58) Field of Classification Search
USPC ......... 604/516, 80, 81, 82, 83, 84, 85, 86, 87, 604/88, 89, 90, 91, 92, 191, 220, 223, 910, 604/68, 71, 181, 187, 218, 233, 257, 258
See application file for complete search history.

(56) References Cited

U.S. PATENT DOCUMENTS 6,332,467 B1 * 12/2001 Hutson et al. ................. 128/877
2004/0152885 A1 * 8/2004 Amegadzie et al. ......... 536/23.5
2007/0060898 A1 * 3/2007 Shaughnessy et al. ....... 604/284
2007/0112323 A1 * 5/2007 Daly .............................. 604/411
2008/0065023 A1 * 3/2008 Kennard ....................... 604/187
2009/0264831 A1 * 10/2009 Thompson et al. ........... 604/191

* cited by examiner

*Primary Examiner* — Kevin C Sirmons
*Assistant Examiner* — Shefali Patel
(74) *Attorney, Agent, or Firm* — Waddey & Patterson, P.C.; Matthew C. Cox; Rebecca M. Barnett

(57) ABSTRACT

A plunger-driven delivery device for use with a feeding tube for delivering an ingestible material to a user is provided. The delivery device includes a device body having a first chamber, a second chamber and an exit orifice through which the ingestible material is delivered to the feeding tube. A first plunger is disposed in the first chamber, and a second plunger is disposed in the second chamber. The delivery device can be provided with the ingestible material disposed in the first chamber and a flushing liquid disposed in the second chamber. The delivery device is operable to provide sequential delivery first of the ingestible material and then the flushing liquid into the feeding tube. In some embodiments, a mechanical interlock is disposed between the first and second plungers to prevent use of the second plunger until the first plunger has been depressed. In additional embodiments, a first passage is defined between the first chamber and the exit orifice and a second passage is defined between the second chamber and the exit orifice. The second passage has a longer passage length than the first passage, allowing delivery of the ingestible material into the feeding tube before the flushing liquid is ejected from the delivery device. A method of delivering an ingestible material to a user through a feeding tube is also provided.

12 Claims, 7 Drawing Sheets

PLUNGER-DRIVEN FEEDING TUBE DELIVERY DEVICE AND METHODS

BACKGROUND

1. Technical Field

The present disclosure relates generally to devices and methods for delivery of ingestible materials to a user's body and more particularly to mechanical devices and methods for delivering ingestible materials to a user's gastrointestinal tract through a feeding tube.

2. Background Art

In many situations, a person or animal can be unable to orally consume ingestible materials such as food products, nutritional supplements or medications and must be intubated with a feeding tube for delivery of such products. Intubation generally involves placing a feeding tube through the mouth or nose of the patient beyond the esophagus and extending to a position in the user's gastrointestinal tract, typically the stomach. A conventional feeding tube typically includes a tube inlet located outside the user's body and a tube outlet positioned inside the user's body. Ingestible materials can be delivered to the user's gastrointestinal tract by injecting such materials into the feeding tube inlet. The ingestible material can then move through the tube and can be ejected from the tube at the tube outlet for consumption by the user.

In many applications, it is desirable to inject the ingestible material through the feeding tube into a user's body using a manual, plunger-driven syringe device. One exemplary application involves the use of a nasogastric feeding tube. A nasogastric feeding tube generally extends through the patient's nostril, nasopharynx, oropharynx, and esophagus leading into the user's stomach or intestine. Devices for delivering ingestible materials to a user through the nasogastric tube inlet using a plunger-driven delivery device, or syringe, are known in the art. Such conventional devices generally include a device having a longitudinal cylindrical chamber, or barrel, defining an interior cavity for storing an ingestible material such as a food product, nutritional supplement or medication. A plunger is typically disposed in the barrel for pushing the ingestible material from the chamber through a device orifice. Conventional devices of this type can include a tube fitting located on or near the device orifice for coupling the device to the nasogastric feeding tube inlet.

One problem associated with conventional plunger-driven feeding tube delivery devices involves incomplete advancement of the ingestible material through the feeding tube. Generally, the feeding tube can have a length from about 10-100 cm, depending on the size of the patient and the particular application. When ingestible material is injected into the nasogastric tube, the material must be pushed through the entire length of the tube to the tube outlet inside the user's body. In some applications, the volume of the ingestible material is less than the interior volume of the feeding tube, and a plunger-driven delivery device is not capable of pushing the entire ingestible material volume completely through the feeding tube using only one stroke of the plunger. Instead, using conventional devices and methods, some ingestible material may remain in the feeding tube after the plunger has been fully depressed in a single stroke, thereby forming an occlusion of ingestible material in the tube and forcing the user to perform additional steps to completely evacuate the tube into the user's stomach. Such additional steps can take many forms and can include disconnecting the delivery device from the tube, retracting the plunger to refill the chamber with a flushing fluid or alternatively providing a new syringe device filled with a flushing liquid, attaching the refilled device to the tube inlet, and injecting the flushing liquid into the tube to force the occlusion of ingestible material through the tube into the user's stomach.

Another problem associated with conventional plunger-driven feeding tube delivery devices includes the growth and development of microorganisms in the feeding tube following passage of the ingestible material through the tube. In some applications, the ingestible material includes chemical compounds that can promote the growth of bacteria in the interior of the tube. Conventional devices can leave ingestible material deposits on the interior wall of the tube following delivery, creating regions that may support bacterial growth. Such bacterial growth can pose health risks to the user as subsequent injections through the tube will likely introduce the bacteria into the user's body. Additionally, because some conventional syringe or plunger-driven devices do not fully evacuate the feeding tube following operation of the plunger, a biofilm can form on the interior of the feeding tube.

Thus, there is a continuing need in the art for improvements in plunger-driven feeding tube delivery devices and methods for introducing ingestible materials into a user's body through a feeding tube.

BRIEF SUMMARY

One aspect of the present invention provides a plunger-driven feeding tube delivery device for injecting ingestible material into a feeding tube. The device includes a device body defining a first chamber, a second chamber and an exit orifice. A first plunger is disposed in the first chamber, the first plunger being moveable between a first retracted position and a first depressed position. A second plunger is disposed in the second chamber, the second plunger being moveable between a second retracted position and a second depressed position. A pivotable interlock is disposed on the device body between the first and second plungers, wherein the interlock engages and prevents movement of the second plunger from the second retracted position to the second depressed position unless the first plunger is in the first depressed position.

Yet another embodiment of the present invention provides a plunger-driven feeding tube delivery device for injecting ingestible material into a feeding tube. The device includes a device body defining a first chamber, a second chamber and an exit orifice shaped for ejecting ingestible material into the feeding tube. A first plunger is disposed in the first chamber, and a second plunger disposed in the second chamber. The device body defines a first passage between the first chamber and the exit orifice, and the first passage includes a first passage length. The device body defines a second passage between the second chamber and the exit orifice, and the second passage includes a second passage length, wherein the first passage length is less than the second passage length.

A further embodiment of the present invention provides a method of administering an ingestible material to a user through a feeding tube. The method includes the steps of: (a) providing a plunger-driven feeding tube delivery device having a first chamber, a second chamber, an exit orifice, a first plunger disposed in the first chamber and a second plunger disposed in the second chamber, the delivery device including an ingestible material contained in the first chamber and a flushing liquid contained in the second chamber; (b) connecting the exit orifice to the feeding tube; and (c) sequentially delivering the ingestible material and then the flushing liquid into the feeding tube.

Numerous other objects, features and advantages of the present disclosure will be readily apparent to those skilled in the art upon a reading of the following description when taken in conjunction with the accompanying drawings.

DETAILED DESCRIPTION

Figure 1:
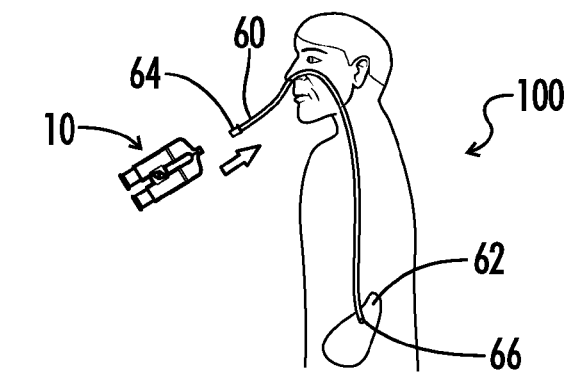
FIG. 1 illustrates a partially exploded view of an embodiment of a plunger-driven feeding tube delivery device in accordance with the present disclosure.

Referring now to the drawings and particularly to FIG. 1, a partially exploded view of an embodiment of a plunger-driven delivery device for a feeding tube is generally shown and is designated by the numeral 10. In the drawings, not all reference numbers are included in each drawing, for the sake of clarity. In addition, positional terms such as "upper," "lower," "side," "top," "bottom," "vertical," "horizontal," etc. refer to the feeding device when in the orientation shown in the drawing. The skilled artisan will recognize that feeding tube delivery devices in accordance with the present disclosure can assume different orientations when in use.

As seen in FIG. 1, a feeding tube 60 is positioned in the body of a user 100. The feeding tube 60 can include an enteral or parenteral feeding tube having a tube inlet 64 and a tube outlet 66. The tube inlet 64 can include an inlet fitting 65 such as a luer connector, a press-fit connector, a threaded connector, a barb connector or any other suitable tube connector, seen in FIG. 5C. Feeding tube 60 in some embodiments, as seen in FIG. 1, includes a nasogastric tube inserted into a nostril of user 100 and extending through the user's gastrointestinal tract to the user's stomach 62. Typically, the tube outlet 66 is positioned in or near the user's stomach 62 and the tube inlet 64 is positioned outside the user's body. Also seen in FIG. 1, in some embodiments, a plunger-driven feeding tube delivery device 10, also referred to as a "delivery device" or a "syringe", can be mechanically connected to the tube inlet 64. The delivery device 10 can be manually actuated by user 100 or by another individual such as a medical professional, nurse, a caretaker, etc. to deliver ingestible material to the user 100 through the feeding tube 60. In some embodiments, user 100 may be unconscious or unable to consume food orally, thus requiring the use of feeding tube 60 for delivery of food products, nutritional supplements, and/or medications.

Figure 2A:
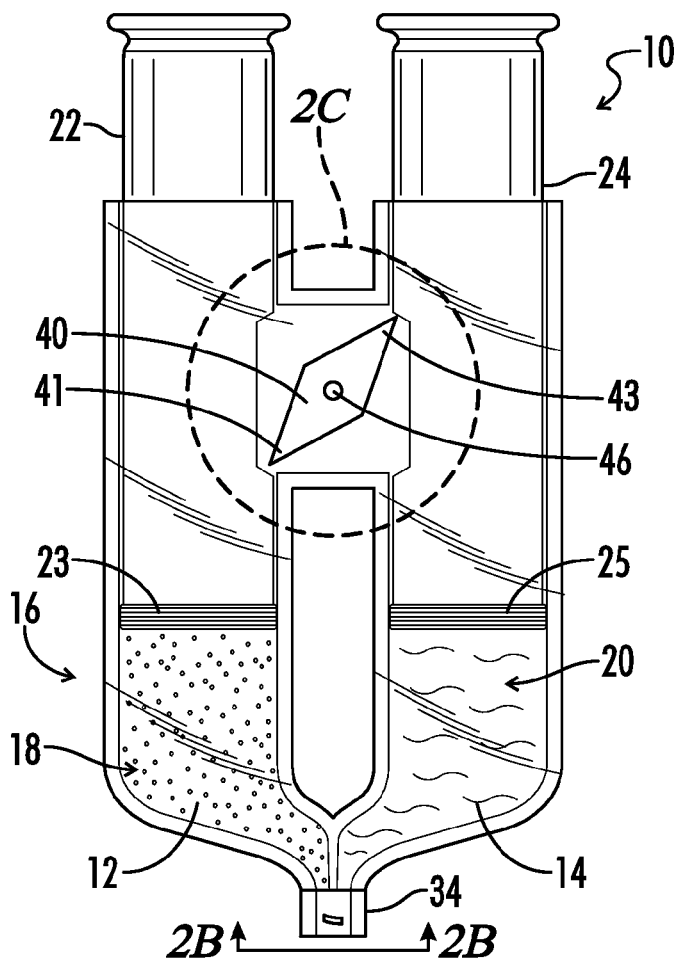
FIG. 2A illustrates a front elevation view of an embodiment of a plunger-driven feeding tube delivery device in accordance with the present disclosure.

Referring now to FIG. 2A, in some embodiments, the present invention provides a delivery device 10 including a device body 16 defining a first longitudinal chamber 18 and a second longitudinal chamber 20. Each chamber defines an interior space enclosed by the device body 16. An exit orifice 26 is defined on the device body 16. Exit orifice 26 generally includes an opening in device body 16 from which ingestible material is ejected. In some embodiments, device body 16 includes a tube fitting 34 adapted to connect delivery device 10 to feeding tube 60, seen in FIG. 1. Tube fitting 34 in some embodiments can include a female luer connector, as seen in FIG. 2A, adapted to engage a corresponding male luer inlet fitting located on tube inlet 64. In other embodiments, tube fitting 34 includes a male luer connector adapted to engage a corresponding female luer inlet fitting located on tube inlet 64 of tube 60. A tube fitting 34 configured to directly engage a feeding tube 60 can be integrally formed on device body 16. In other embodiments, as seen in FIG. 5C, device body 16 does not include an integrally formed tube fitting, and a tube adapter 84 can be used to connect device body 16 to feeding tube 60. Tube adapter 84 can include a barrel-shaped adapter having a central aperture shaped for the passage of material and a first adapter end operable to engage device body 16. For example, the device body can include a threaded region 82 located near exit orifice 26. Tube adapter 84 can include corresponding threads that threadedly engage threaded region 82 on device body 16 allowing tube adapter 84 to be screwed onto device body 16. Tube adapter 84 can also include a second adapter end including an adapter fitting 86 operable to engage feeding tube 60. In some embodiments, adapter fitting 86 is configured to engage inlet fitting 65 on feeding tube 60. Adapter fitting 86 can include a luer connector, press-fit connector, barbed connector, threaded connector or any other suitable type of tube connector known in the art. Different styles and sizes of feeding tubes can exist. Tube adapter 84 allows a single model of delivery device 10 to be used interchangeably with different sizes and styles of feeding tubes 60 having various inlet fittings 65. In some embodiments, the present invention provides a kit including a device body 16 and a plurality of tube adapters 84 configured to engage various feeding tube inlet fittings. In further embodiments, tube adapter 84 includes a second adapter end having a closed surface. In such embodiments, tube adapter 84 can be attached to device body 16 to close, or to plug, exit orifice 26 and to seal first and second chambers 18, 20 for transport or for later use.

Referring further to FIG. 2A, a first plunger 22 is disposed in the first chamber 18, and a second plunger 24 is disposed in the second chamber 20. Each plunger can be longitudinally moved within each corresponding chamber to eject a substance from the exit opening 26 into a feeding tube. In some embodiments, first plunger 22 includes a first plunger seal 23 for sealing first chamber 18. Additionally, second plunger 24 includes a second plunger seal 25 for sealing second chamber 20. Each plunger 22, 24 generally includes a retracted position and a depressed position. In the embodiment illustrated in FIG. 2A, each plunger 22, 24 is shown in a retracted position. First plunger 22 is moveable from the first retracted position, seen in FIG. 2A, to the first depressed position seen in an embodiment in FIG. 3A. Similarly, second plunger 24 is moveable from the second retracted position, seen in FIG. 2A, to the second depressed position seen in an embodiment in FIG. 4.

Each chamber 18, 20 includes a chamber volume and a chamber diameter. In some embodiments, the first chamber diameter and the second chamber diameter are about the same. In other embodiments, it may be advantageous to provide first and second chambers 18, 20 having different diameters. In such embodiments, when first and second plungers 20, 22 are depressed simultaneously, different flowrates and material volumes can be ejected from each respective chamber simultaneously. Additionally, in some embodiments, it may be desirable to provide a device having first and second chambers of differing lengths.

Referring again to FIG. 2A, in some embodiments, a pivotable interlock 40 is disposed on the device body 16 between the first and second plungers 22, 24. Interlock 40 engages and prevents movement of the second plunger 24 from the second retracted position to the second depressed position unless the first plunger 22 is in the first depressed position. Referring to FIG. 2C, interlock 40 in some embodiments includes a first interlock end 41 and a second interlock end 43. Each interlock end 41, 43 extends from a pivot 46, or axle, about which interlock 40 is pivotally mounted. Pivot 46 in some embodiments is integrally formed on device body 16. First interlock end 41 extends toward first plunger 22 and second interlock end 43 extends toward second plunger 24. As seen in FIG. 2D, in some embodiments, interlock 40 includes a spring 48 disposed between interlock 40 and device body 16. Spring 48 can include a coil spring disposed about pivot 46. In some embodiments, spring 48 is a torsion spring having a first spring end 49a attached to the interlock 40 and a second spring end 49b attached to the device body 16. The torsion spring 48 is positioned such that second interlock end 43 is biased toward second plunger 24, and first interlock end 41 is biased toward first plunger 22, as seen in FIG. 2C.

Referring further to FIG. 2A and FIG. 2C, first plunger 22 in some embodiments defines a first plunger recess 42 substantially facing interlock 40. Similarly, second plunger 24 defines a second plunger recess 44 substantially facing interlock 40. Second plunger recess 44 defines a second recess surface 47 adjacent second plunger recess 44. In some embodiments, second interlock end 43 extends partially into second plunger recess 44 and engages second recess surface 47, thereby preventing movement of second plunger 24 toward exit orifice 26 when first plunger 22 is in the first retracted position.

Referring further to FIG. 2C, when the first and second plungers are both in the retracted position, first interlock end 41 partially extends into first plunger recess 42, and second interlock end 43 partially extends into second plunger recess 44. Because second interlock end 43 engages second recess surface 47, second plunger 24 cannot be pushed in or moved from the second retracted position to the second depressed position unless the second interlock end 43 is disengaged from the second recess surface 47. Although the embodiment seen in FIG. 2A and FIG. 2C illustrates a second recess surface 47 having an inclined shape, it is understood that second recess surface 47 can have various other suitable shapes and orientations for engaging interlock 40. As seen in FIG. 2C, in some embodiments, second recess surface 47 is oriented at a second recess surface angle 59 relative to the longitudinal axis of second plunger 24. Second recess surface angle 59 can range between about thirty degrees and about one-hundred fifty degrees. In a preferred embodiment, second recess surface angle 59 can range between about sixty degrees and about one-hundred twenty degrees.

Figure 3A:
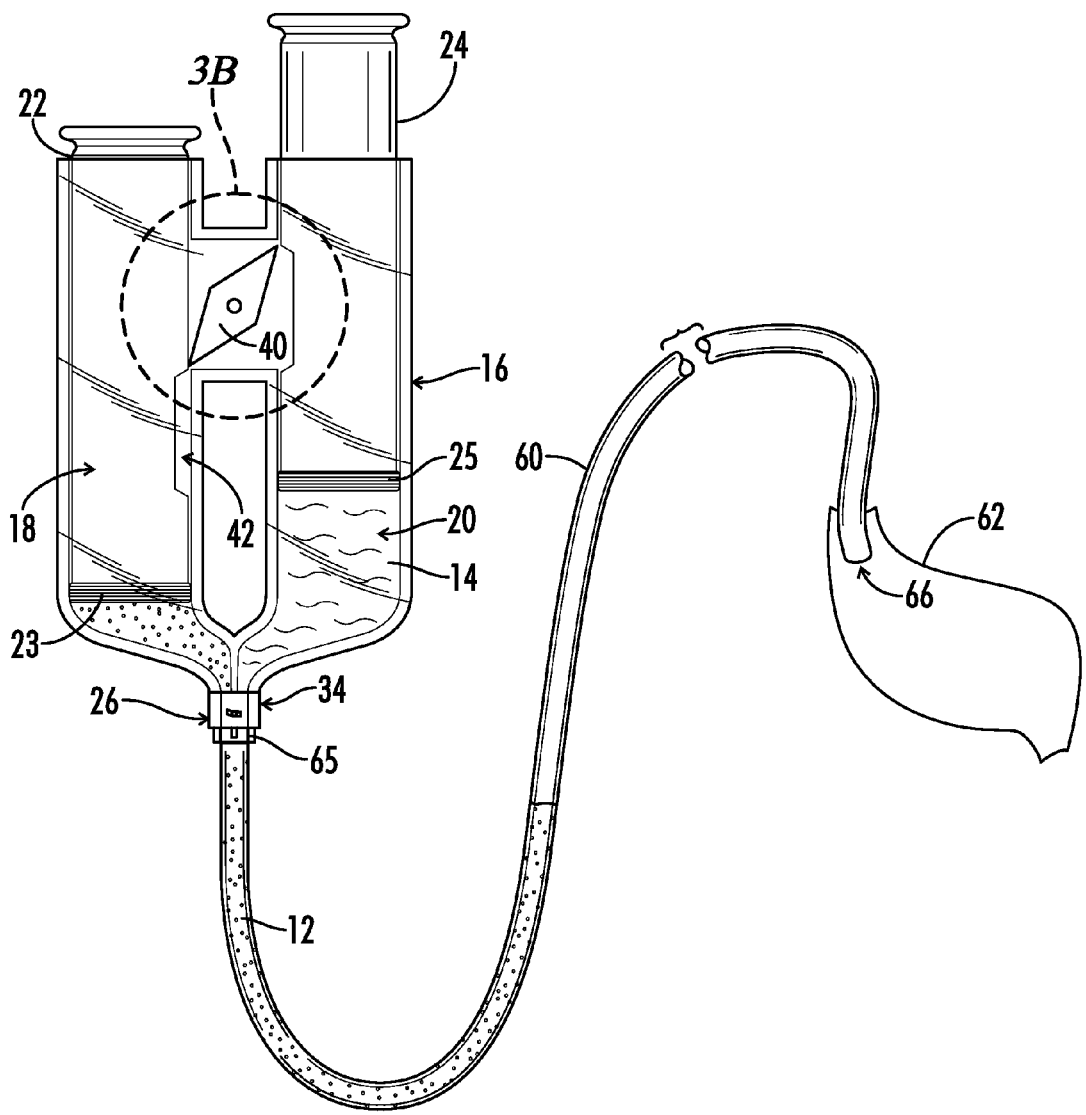
FIG. 3A illustrates a partial perspective view of an embodiment of a plunger-driven feeding tube delivery device with a first plunger in a first fully depressed position and a second plunger in a second retracted position in accordance with the present disclosure.

Referring now to FIG. 3A, in some embodiments, first plunger 22 can be moved from the first retracted position seen in FIG. 2A to the first depressed position, seen in FIG. 3A, while second plunger 24 remains in the second retracted position. Before first plunger 22 is depressed, delivery device 10 can be attached to feeding tube 60 by connecting tube fitting 34 or adapter fitting 86 to inlet fitting 65.

When first plunger 22 is moved to the first depressed position, as seen in FIG. 3A, ingestible material 12 contained in first chamber 18 is ejected from exit orifice 26 on device body 16 and enters feeding tube 60. In some embodiments, the volume of ingestible material 12 ejected from delivery device 10 does not pass completely through feeding tube 60 to the stomach 62. Instead, some ingestible material 12 may form an occlusion in feeding tube 60, as illustrated in FIG. 3A. Thus, it may be necessary to subsequently inject a flushing liquid 14 into feeding tube 60 to flush the ingestible material 12 completely through feeding tube 60 and out tube outlet 66 into stomach 62. However, in some embodiments, before second plunger 24 can be depressed, interlock 40 must be disengaged from second plunger 24.

Figure 3B:
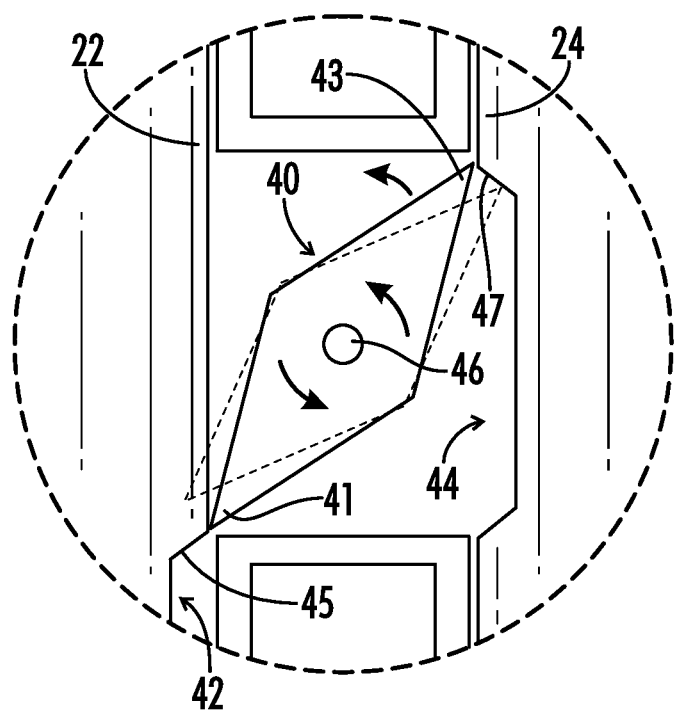
FIG. 3B illustrates a detail elevation view of Section 3B from FIG. 3A showing an embodiment of a mechanical interlock in a disengaged position in accordance with the present disclosure.

Referring now to FIG. 3A and FIG. 3B, in some embodiments, an interlock release surface 45 is defined on first plunger 22. In some embodiments, interlock release surface 45 is located adjacent plunger recess 42. In other embodiments, interlock release surface 45 can be located at other positions on first plunger 22. Interlock 40 is positioned on device body 16 such that interlock release surface 45 engages first interlock end 41 when first plunger 22 moved to the first depressed position. When interlock release surface 45 engages first interlock end 41, interlock 40 rotates about pivot 46, causing second interlock end 43 to disengage from second recess surface 47 and to move away from second plunger recess 44, thereby freeing second plunger 24 for movement from the second retracted position to the second depressed position. Disengagement of interlock 40, also referred to as angular movement of interlock 40 following engagement of first interlock end 41 by interlock release surface 45, is illustrated in an embodiment in FIG. 3B.

Figure 4:
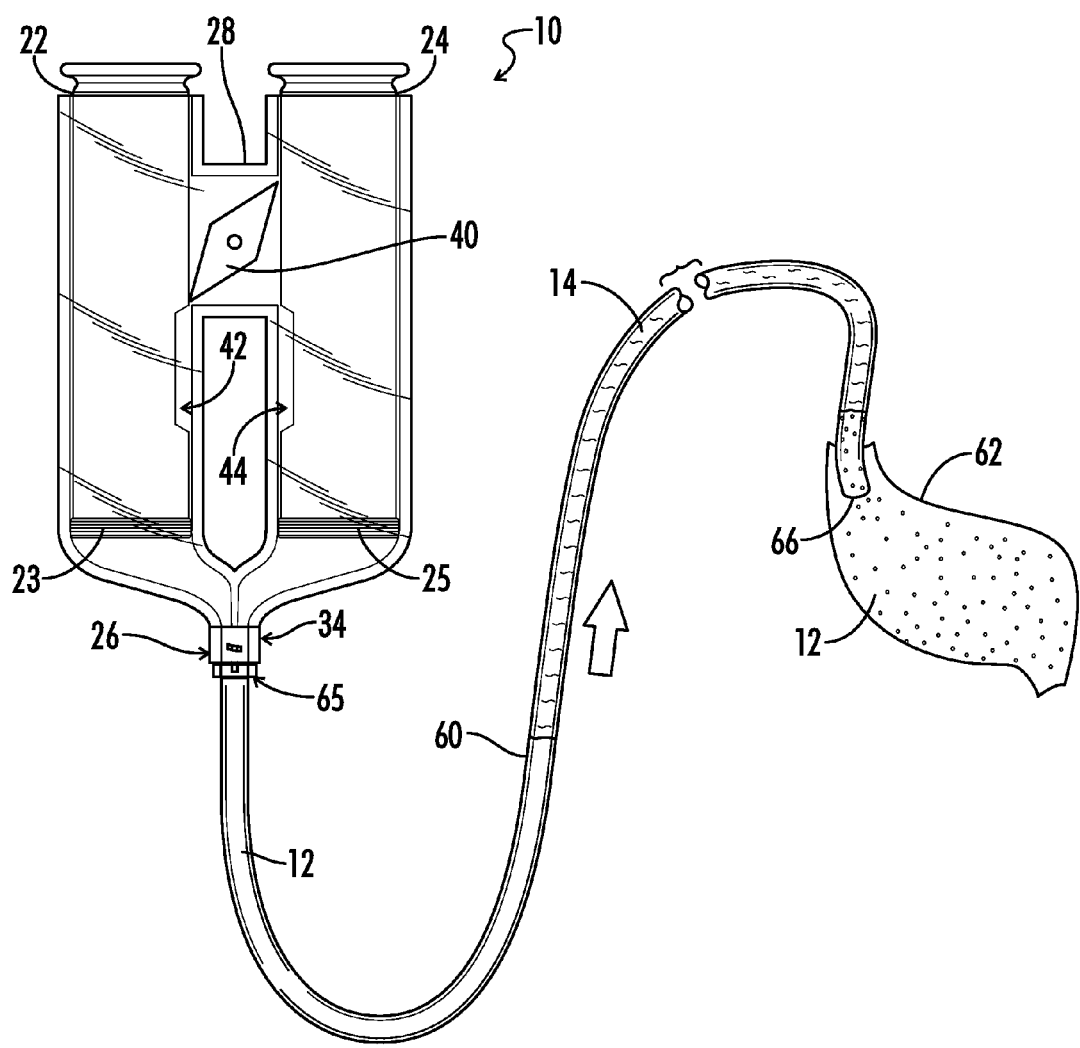
FIG. 4 illustrates an embodiment of a plunger-driven feeding tube delivery device with a first plunger in a first depressed position and a second plunger in a second depressed position in accordance with the present disclosure.

Referring now to FIG. 4, when interlock 40 is disengaged, second plunger 24 can be moved from second retracted position to second depressed position, forcing flushing liquid 14 through tube 60. When flushing liquid 14 enters tube 60, flushing liquid 14 can push ingestible material 12 into the stomach 62. Also, in some applications, flushing liquid 14 can lubricate feeding tube 60, allowing ingestible material 12 to slide more easily through feeding tube 60 into stomach 62. Flushing liquid 14 can also partially dissolve ingestible material 12, further facilitating travel of ingestible material 12 through feeding tube 60 into stomach 62.

In some embodiments, ingestible material 12 includes a food product, a nutritional supplement and/or a pharmaceutical compound or medication. In some embodiments, ingestible material 12 is a solid. In other embodiments, ingestible material 12 can include a powder or particulate material that is intended to be mixed with flushing liquid 14. In other embodiments, ingestible material 12 can include an amorphous solid such as a gel or a paste. One or more nondigestible prebiotic materials that promote the growth and development of bacteria in the digestive tract, such as but not limited to a galactooligosaccharide (GOS) or a fructooligosaccharide (FOS), can also be included in ingestible material 12 in some embodiments. Other suitable prebiotic or probiotic materials and mixtures known in the art can be included in ingestible material 12 in some embodiments.

The presence of ingestible material 12 in feeding tube 60 can contribute to the growth and development of bacteria on the inner tube wall. Such bacterial growth and development presents a threat of contamination to the user and is generally undesirable. Additionally, after one or more uses, tube 60 may develop a biofilm on the interior tube wall. Such a biofilm may include one or more types of bacteria and can pose a health hazard to the user. Bacteria and biofilm growth and development can be prevented by forcing a flushing liquid 14 through tube 60 following passage of ingestible material 12 through feeding tube 60. Flushing liquid 14 contained in second chamber 20 can perform one or more functions when injected into the feeding tube 60. First, flushing liquid 14 can push ingestible material 12 through feeding tube 60 into the user's stomach 62. Second, flushing liquid 14 can disinfect the interior feeding tube wall to inhibit bacterial growth and development. Third, flushing liquid 14 can prevent biofilm growth and development on the interior feeding tube wall. It is understood that flushing liquid 14 can perform as few as one or as many as all of these functions in various embodiments.

In some embodiments, flushing liquid 14 comprises water. In further embodiments, flushing liquid 14 includes a disinfectant material or an antimicrobial agent for killing and/or preventing the growth of microorganisms such as bacteria in tube 60.

As seen in FIG. 4, after second plunger 24 is moved to the second depressed position, flushing liquid 14 travels through feeding tube 60 and enters stomach 62. At this point, delivery device 10 can be disconnected from feeding tube 60 and discarded in some embodiments. In other embodiments, delivery device 10 can be disconnected from feeding tube 60 and refilled or stored for future reuse.

Figure 5A:
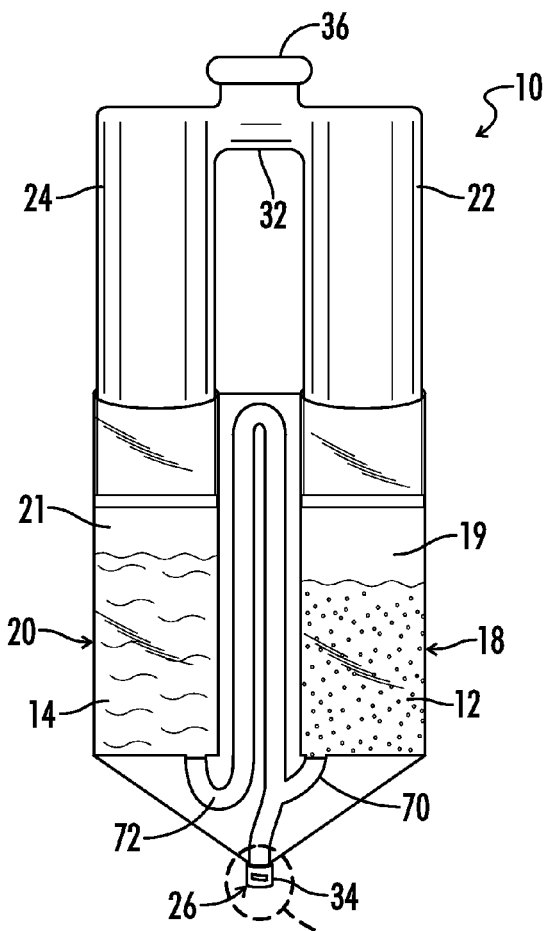
FIG. 5A illustrates a perspective view of a second embodiment of a plunger-driven feeding tube delivery device having a first plunger in a first retracted position and a second plunger in a second retracted position in accordance with the present disclosure.
Figure 5B:
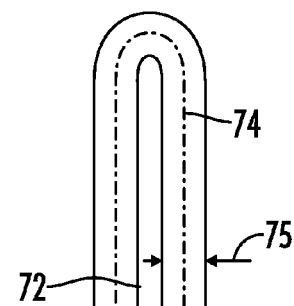
FIG. 5B illustrates a detail view of an embodiment of a plunger-driven feeding tube delivery device showing first and second passages in accordance with the present disclosure.
Figure 5C:
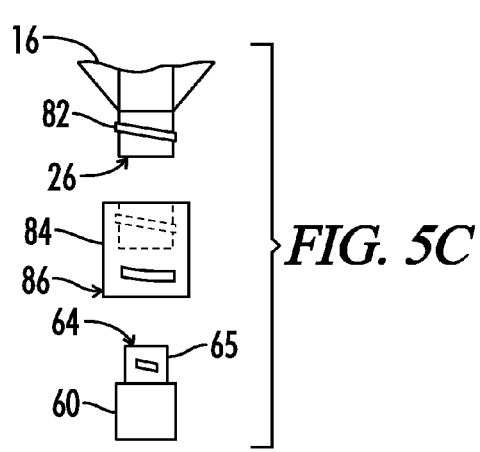
FIG. 5C illustrates a partial exploded view of an embodiment of a feeding tube delivery device from FIG. 5A showing a tube adapter.

Referring now to FIG. 5A, in yet another embodiment, a plunger-driven feeding tube delivery device 10 includes a device body 16 defining a first chamber 18, a second chamber 20 and an exit orifice 26 shaped for ejecting ingestible material into a feeding tube. In some embodiments, a first plunger 22 is disposed in the first chamber 18 and a second plunger 24 is disposed in the second chamber 20. The device body 16 defines a first passage 70 extending between the first chamber 18 and the exit orifice 26. The device body 16 also defines a second passage 72 extending between the second chamber 20 and the exit orifice 26. As seen in FIG. 5B, the first passage 70 includes a first passage length 78, and second passage 72 includes a second passage length 74. In some embodiments, the first passage length 78 is less than the second passage length 74. In further embodiments, the ratio of the second passage length 74 to the first passage length 78 is greater than about two. In other embodiments, the ratio of the second passage length 74 to the first passage length 78 is greater than about five.

As seen in FIG. 5A, an ingestible material 12 can be disposed in the first chamber 18 and a flushing liquid 14 can be disposed in the second chamber 20. In some embodiments, first plunger 22 is attached to second plunger 24 by a plunger bridge 32. Plunger bridge 32 allows both first and second plungers 22, 24 to be simultaneously depressed using a single plunger knob 36. During use, the device body 16 can be held in one hand by an operator while plunger knob 36 is depressed using the other hand, thereby forcing first and second plungers simultaneously toward exit orifice 26 and dispensing one or more materials from first and second chambers.

Figure 5D:
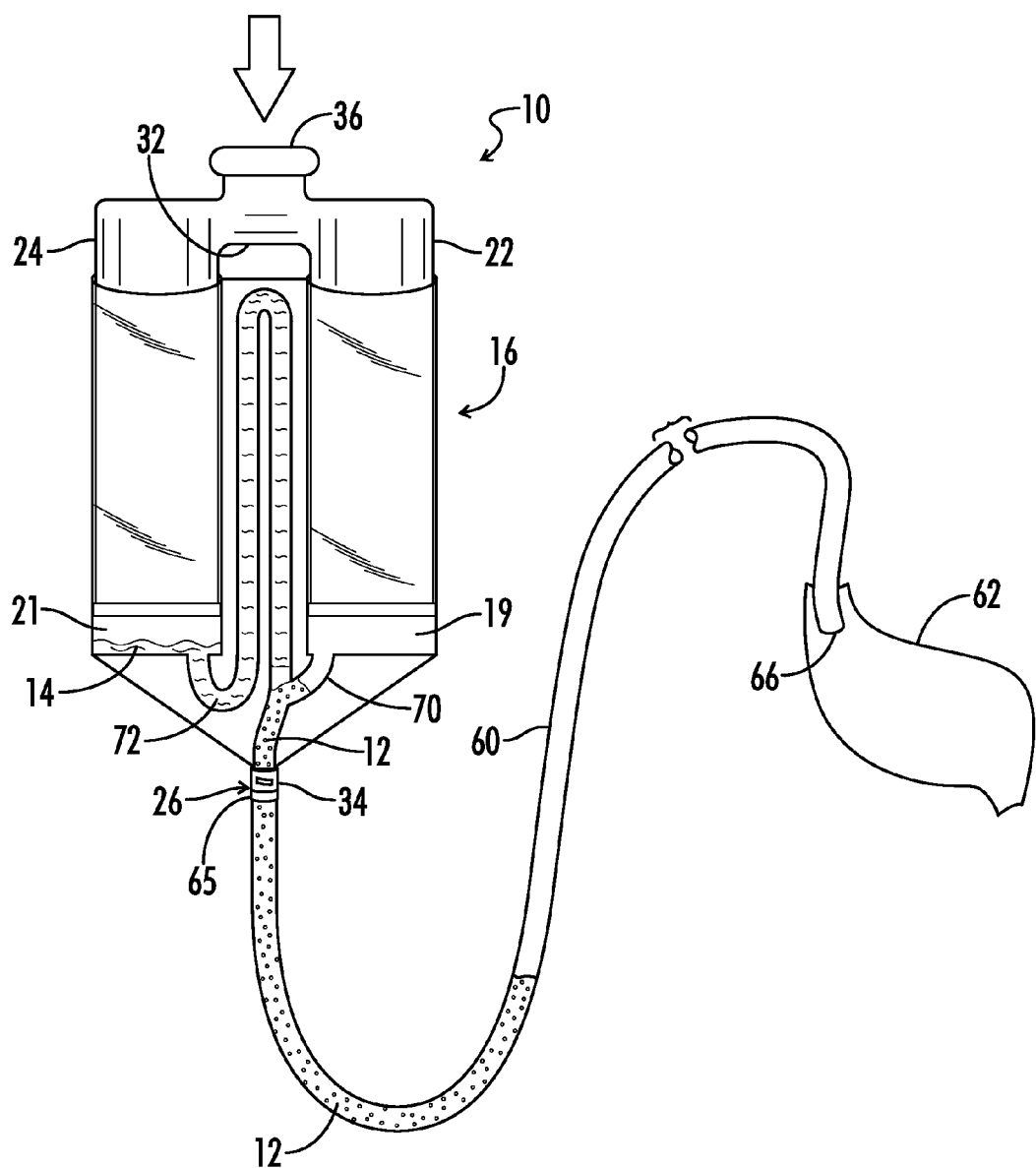
FIG. 5D illustrates a perspective view of an embodiment of the plunger-driven feeding tube delivery device of FIG. 5C showing the first and second plungers each in a depressed position in accordance with the present disclosure.

In some embodiments, delivery device 10 is adapted to not dispense the flushing liquid 14 until some or all of ingestible material 12 has been dispensed. For example, referring to FIG. 5D, when first and second plungers 22, 24 are depressed together, ingestible material 12 is pushed through first passage 70 out exit orifice 26 into feeding tube 60 toward stomach 62. Simultaneously, flushing liquid 14 is pushed through second passage 72. Because second passage 72 includes a second passage length 74 longer than first passage length 78, flushing liquid 14 does not reach exit orifice 26 until some or all of ingestible material 12 has entered feeding tube 60. Thus, in some embodiments, delivery device 10 is capable of sequentially delivering ingestible material 12 followed by flushing liquid 14 into feeding tube 60 using only a single, simultaneous stroke of first and second plungers 22, 24.

Referring further to FIG. 5A, in some embodiments, first passage 70 can include a partial amount of ingestible material 12 after first plunger 22 is moved to the first depressed position. This may be undesirable in some applications. To overcome this problem, in some embodiments, a first gas pocket 19 can be included in first chamber 18 between first plunger seal 23 and ingestible material 12. The first gas pocket 19 can include a gas volume similar to the volume of the first passage 70. Thus, when first plunger 22 is moved to the first depressed position, first gas pocket 19 is forced through first passage 70, thereby pushing any residual ingestible material 12 out of first passage 70.

Similarly, in some embodiments, second passage 72 can include a partial amount of flushing liquid 14 disposed therein after second plunger 24 is moved to the second depressed position. This may be undesirable in some applications. To overcome this problem, in some embodiments, a second gas pocket 21 can be included in second chamber 20 between second plunger seal 25 and flushing liquid 14. Second gas pocket 21 can include a gas volume similar to the volume of the second passage 72. Thus, when second plunger 24 is moved to the second depressed position, second gas pocket 21 is forced through second passage 72, thereby pushing any residual flushing liquid 14 out of second passage 72. First and second gas pockets 19, 21 can include a sterile, inert gas in some embodiments.

Referring again to FIG. 2A and FIG. 5A, in some embodiments, a first gas pocket 19 and/or a second gas pocket 21, as seen in FIG. 5A, can be disposed in first and second chambers 18, 20, respectively, in an embodiment having an interlock 40, as seen in FIG. 2A. For example, ingestible material 12 can be provided in a device as seen in FIG. 2A with a first gas pocket 19 positioned between first plunger seal 23 and ingestible material 12. Similarly, in some embodiments, flushing liquid 14 can be provided in a device as seen in FIG. 2A with a second gas pocket 21 positioned between second plunger seal 25 and flushing liquid 14. It is understood, that in some embodiments, a gas pocket is provided in both chambers. In other embodiments, a gas pocket is provided in only one chamber. For example, in some embodiments, ingestible material 12 is relatively viscous, and second chamber 18 of a device as illustrated in FIG. 2A includes a flushing liquid 14 and second gas pocket disposed between second plunger seal 25 and flushing liquid 14. In such embodiments, a second gas pocket may be necessary to force both flushing liquid 14 and ingestible material 12 completely through the feeding tube.

In some embodiments, the plunger-driven feeding tube delivery device 10 of the present invention is a disposable, single-use syringe. The delivery device 10 can be provided in a sanitary package and can be pre-filled with ingestible material 12 and flushing liquid 14. In other embodiments, delivery device 10 can include a reusable and refillable syringe. In some embodiments, interlock 40 is exposed so that a user can manually manipulate the angular position of interlock 40 for removing first and/or second plungers 22, 24 from device body 16 for cleaning or refilling.

Figure 2B:
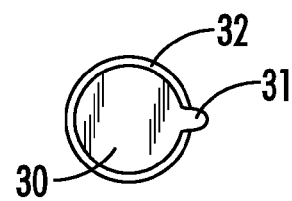
FIG. 2B illustrates an end view of Section 2B-2B of an embodiment of the delivery device of FIG. 2A.
Figure 2C:
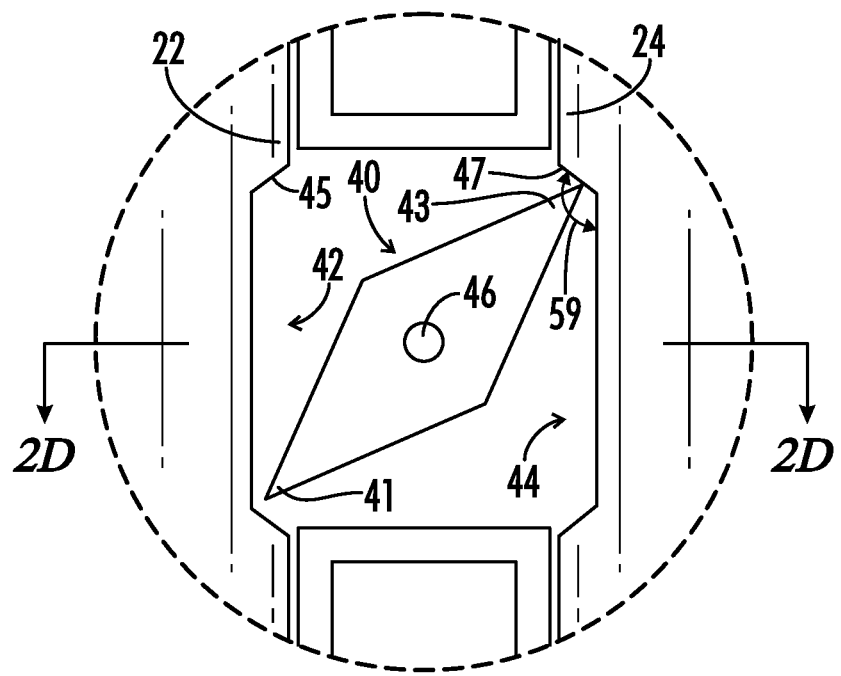
FIG. 2C illustrates a detail elevation view of an embodiment of a mechanical interlock of the device of FIG. 2A in an engaged position.
Figure 2D:
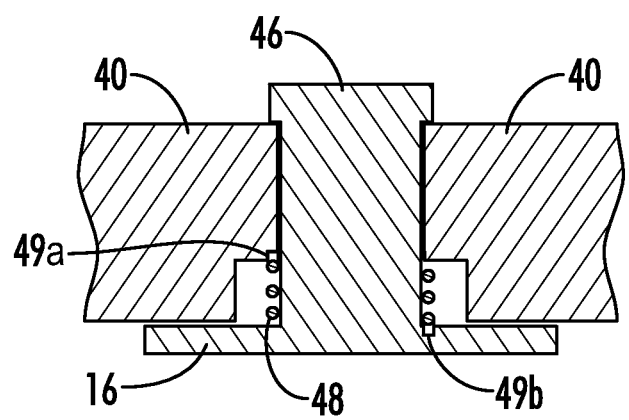
FIG. 2D illustrates a partial cross-sectional view of Section 2D-2D from FIG. 2C showing an embodiment of an interlock in accordance with the present disclosure.

In some embodiments, as seen in FIG. 2B, the delivery device 10 includes a removable seal 30 covering exit orifice 26. The removable seal 30 can be manually removed by a user prior to use. In some embodiments, removable seal 30 includes a seal tab 31 radially protruding from the perimeter of seal 30 for manually peeling seal 30 from tube fitting 34. In other embodiments, delivery device 10 is provided with a removable cap covering exit orifice 26 and sealing delivery device 10 from contamination prior to use.

Additionally, as previously noted, in some embodiments, one or both chambers 18, 20 can include a pharmaceutical ingredient. In some embodiments, a first pharmaceutical ingredient having a first time release rate can be disposed in ingestible material 12 in the first chamber 18. Similarly, in some embodiments, a second pharmaceutical ingredient having a second time release rate can be disposed in the second chamber 20 as a second ingestible material in place of flushing liquid 14. In some embodiments, only one pharmaceutical ingredient is disposed in the device. One embodiment provides a first pharmaceutical ingredient with a first release rate disposed in the first chamber and a second pharmaceutical ingredient of the same pharmaceutical compound but with a second release rate disposed in the second chamber, wherein the first release rate is faster than the second release rate. As such, the first pharmaceutical release rate is designated to be delivered from the device into the feeding tube first, and the second pharmaceutical ingredient is designated to be delivered into the feeding tube second. In such embodiments, in some applications, a second gas pocket can be disposed in the second chamber to flush the second pharmaceutical ingredient from the device through the feeding tube into the user's stomach. Such an embodiment can provide the user with a smoother, longer-lasting dose of the same drug by sequentially delivering first a fast release dose of the drug, followed by an extended release dose of the same drug.

In another embodiment, two different pharmaceutical compounds may be used to tread a certain indication. When the two different compounds are manufactured or provided in a single container, the compounds may become unstable or have a tendency to chemically react. One way to overcome this problem is to provide a device in accordance with the present invention having the first pharmaceutical compound disposed in the first chamber 18 and the second pharmaceutical compound disposed in the second chamber 20. In such embodiments, the first pharmaceutical compound will be spatially separated from the second pharmaceutical compound until the first and second plungers are depressed to deliver both compounds to the user through the feeding tube. Additionally, in such embodiments, a gas pocket can be disposed in the second chamber to provide a gas flush for the second pharmaceutical compound. It is understood that the first and second pharmaceutical compounds can be suspended or contained in another material, such as an ingestible solid or liquid.

A further embodiment of the present invention provides a method of administering an ingestible material to a user through a feeding tube. In some embodiments, the method includes the steps of: (a) providing a plunger-driven feeding tube delivery device having a first chamber, a second chamber, an exit orifice, a first plunger disposed in the first chamber and a second plunger disposed in the second chamber, the delivery device including an ingestible material contained in the first chamber and a flushing liquid contained in the second chamber; (b) connecting the exit orifice to the feeding tube; and (c) sequentially delivering the ingestible material then the flushing liquid into the feeding tube. In some embodiments, the first and second plungers are mechanically linked by plunger bridge 32.

In further embodiments, step (c) of the method further includes the steps of: (c1) depressing the first plunger, dispensing the ingestible material into the feeding tube; and (c2) depressing the second plunger after the first plunger has been depressed, dispensing the flushing liquid into the feeding tube. In some embodiments, the delivery device includes a first passage positioned between the first chamber and the exit orifice, and the device also defines a second passage between the second chamber and the exit orifice. The first passage includes a first passage length, and the second passage includes a second passage length, wherein the second passage length is greater than the first passage length. In this embodiment, step (c) further includes the steps of: (c1) simultaneously depressing the first and second plungers; (c2) forcing the ingestible material through the exit orifice into the feeding tube; and (c3) forcing the flushing liquid through the second passage.

In an additional embodiment, the present invention provides a method of packaging a plunger-driven feeding tube delivery device. The method includes the steps of: (a) providing a device body having a first chamber, a second chamber, an exit orifice; (b) filling the first chamber with an ingestible material; (c) filling the second chamber with a flushing liquid; (d) positioning a first plunger in the first chamber; (e) positioning a second plunger in the second chamber; (f) positioning an interlock between the first and second plungers; and (g) engaging the second plunger with the interlock so that the second plunger cannot be depressed until the first plunger has been depressed.

Thus, although there have been described particular embodiments of the present invention of a new and useful Plunger-Driven Feeding Tube Delivery Device and Methods, it is not intended that such references be construed as limitations upon the scope of the invention except as set forth in the following claims.

What is claimed is:

1. A plunger-driven feeding tube delivery device for injecting an ingestible material into a feeding tube, the device comprising:
   a device body defining a first chamber, a second chamber and an exit orifice;
   a first plunger disposed in the first chamber, the first plunger being moveable between a first retracted position and a first depressed position, the first plunger defining a first plunger recess;
   a second plunger disposed in the second chamber, the second plunger being moveable between a second retracted position and a second depressed position, the second plunger defining a second plunger recess having an interlock engagement surface;
   a pivotable interlock disposed on the device body between the first and second plungers;
   a pivot disposed on the device body, the pivotable interlock being pivotally attached to the pivot;
   the pivotable interlock including a first interlock end projecting toward the first plunger recess and a second interlock end projecting toward the second plunger recess; and the second interlock end engaging the interlock engagement surface when the second plunger is in the second retracted position,
wherein the pivotable interlock engages and prevents movement of the second plunger from the second retracted position to the second depressed position until the first plunger is moved to the first depressed position.

2. The device of claim 1, further comprising:
the ingestible material disposed in the first chamber; and
a flushing liquid disposed in the second chamber.

3. The device of claim 2, wherein the ingestible material includes a food product.

4. The device of claim 2, wherein the ingestible material includes a nutritional supplement.

5. The device of claim 2, wherein the ingestible material includes a pharmaceutical compound.

6. The device of claim 2, wherein the flushing liquid comprises an antimicrobial agent.

7. The device of claim 2, wherein the flushing liquid comprises water.

8. The device of claim 1, further comprising a tube fitting disposed on the device body adjacent the exit orifice.

9. The device of claim 8, wherein the tube fitting further comprises a luer connector.

10. The device of claim 8, further comprising a nasogastric feeding tube connected to the tube fitting.

11. The device of claim 1, further comprising:
the first plunger defining an interlock release surface adjacent the first plunger recess, the interlock release surface positioned to engage the first interlock end when the first plunger is in the first depressed position.

12. The device of claim 1, further comprising a spring disposed about the pivot, the spring angularly biasing the first interlock end toward the first plunger.

* * * * *